United States Patent [19]

Sato et al.

[11] Patent Number: 5,033,472
[45] Date of Patent: Jul. 23, 1991

[54] METHOD OF AND APPARATUS FOR ANALYZING PROPAGATION OF ARTERIAL PULSE WAVES THROUGH THE CIRCULATORY SYSTEM

[75] Inventors: Toru Sato; Naoto Okazaki, both of Yonago; Hironami Kubota, Chofu; Hitoshi Suzuki, Tama, all of Japan

[73] Assignees: Nihon Kohden Corp., Shinjuku, Tokyo, Japan; Toru Sato, Yonago, Japan

[21] Appl. No.: 314,707

[22] Filed: Feb. 23, 1989

[51] Int. Cl.$^5$ ............................................... A61B 5/02
[52] U.S. Cl. .................................... 128/691; 128/687; 128/700
[58] Field of Search ............... 128/687, 688, 689, 690, 128/691, 667, 671, 700, 708, 28

[56] References Cited

U.S. PATENT DOCUMENTS

| | | | |
|---|---|---|---|
| 2,944,542 | 7/1960 | Barnett et al. | 128/671 |
| 3,608,545 | 9/1971 | Novack et al. | 128/700 |
| 3,734,086 | 5/1973 | Phelps, Sr. | 128/687 |
| 3,742,938 | 7/1973 | Stern | 128/687 |
| 3,871,360 | 3/1975 | Van Horn et al. | 128/671 |
| 4,425,922 | 1/1984 | Conti et al. | 128/700 |
| 4,510,944 | 4/1985 | Porges | 128/687 |
| 4,545,387 | 10/1985 | Balique | 128/687 |
| 4,802,486 | 2/1989 | Goodman et al. | 128/687 |

FOREIGN PATENT DOCUMENTS 0021800 1/1981 European Pat. Off. ............ 128/700

OTHER PUBLICATIONS

Almasi et al., "Basic Tech. of Voluntary Cardiorespiratory Synch. in Electrocardiology," IEEE; vol. BME-21, No. 4, July 1974; pp. 264-273.

*Primary Examiner*—William E. Kamm
*Assistant Examiner*—Kennedy J. Schaetzle
*Attorney, Agent, or Firm*—Hoffmann & Baron

[57] ABSTRACT

Method and apparatus for analyzing the propagation of arterial pulse waves in a patient's circulatory system. The apparatus comprises R-wave detecting means for outputting an R-wave timing signal at the time of detection of the R-wave component contained in a detected electrocardiographic signal. A pulse wave peak detecting means is provided for outputting a peak timing signal at the time of the detection of a selected peak of the arterial pulse wave detected in the peripheral blood vessels of a patient's circulatory system. A pulse wave propagation time counter is provided for successively counting the time interval from the input of the R-wave timing signal to the input of the peak timing signal, and a pulse wave propagation time analyzer is provided for analyzing the distribution of pulse wave propagation times and other detected biophysiological parameters, from which an effective diagnosis of the condition of the patient's circulatory system can be made.

7 Claims, 4 Drawing Sheets

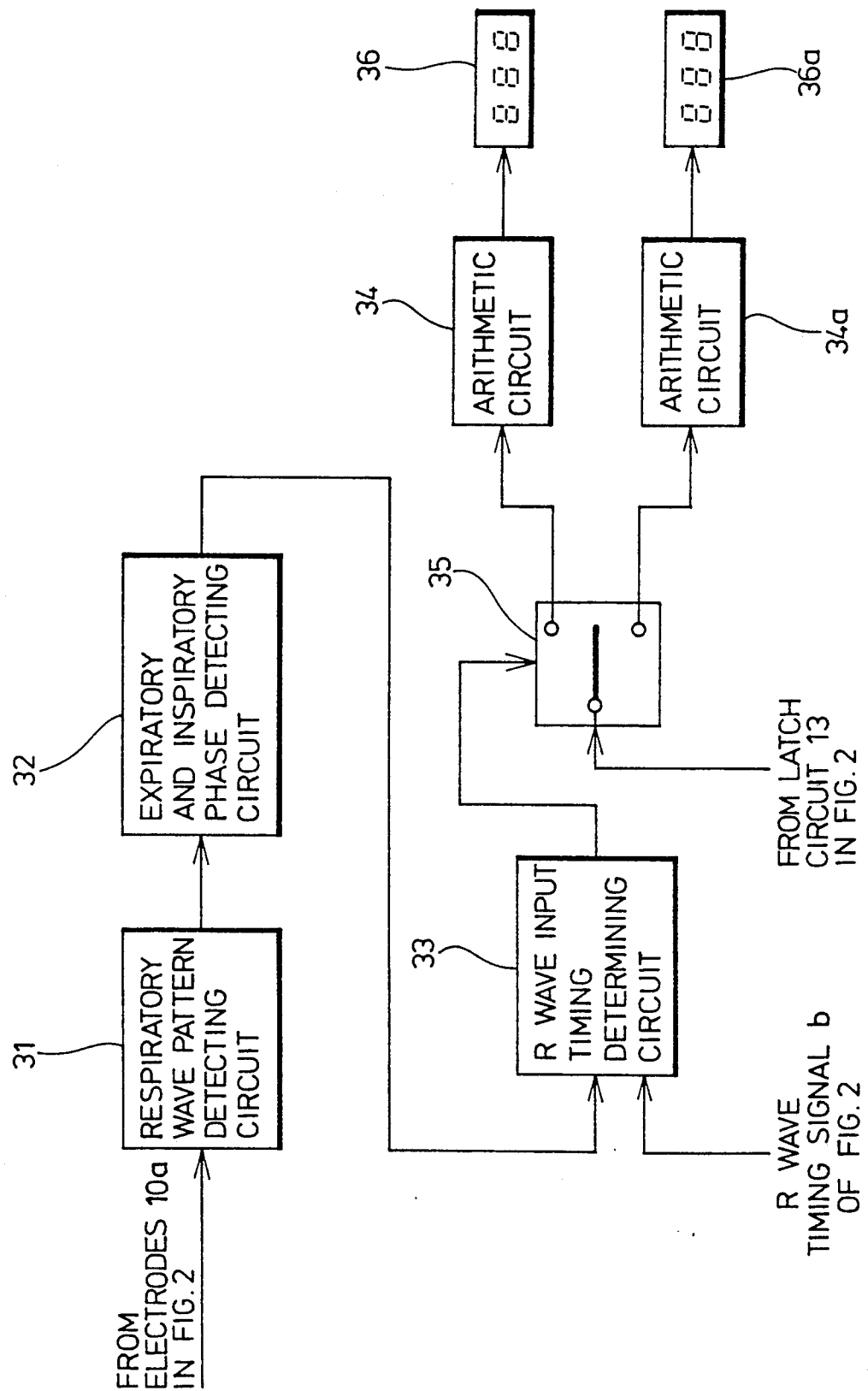

METHOD OF AND APPARATUS FOR ANALYZING PROPAGATION OF ARTERIAL PULSE WAVES THROUGH THE CIRCULATORY SYSTEM

BACKGROUND OF THE INVENTION

This invention relates to an apparatus for analyzing the propagation of arterial pulse waves through vascular vessels in order to diagnose circulatory diseases by analyzing the nature of arterial pulse wave propagation through the circulatory system, i.e. from the heart to the peripheral portions of the circulatory system and the like.

Methods of analyzing the speed of wave propagation as a pulse wave propagates through an artery, is generally known. In such prior art methods, waveforms of a phonocardiogram (PKG) or an electrocardiogram (EKG) and selected forms of pulse waves are simultaneously drawn on the same recording paper. Each waveform is analyzed, and the distance between specific positions along the circulatory system is measured by using a scale. The obtained results are converted into the time taken for the pulse wave to propagate from the center (i.e. heart) to the periphery of the circulatory system, and the speed of the propagating arterial pulse wave is measured using the above-described propagation-length compensation procedure.

Japanese Patent Publication No. 6930/1982 discloses another type of apparatus for measuring the speed of an arterial pulse wave. In order to save labor and time necessary to compute the speed of an arterial pulse wave for each occurrence of arterial pulse wave propagation, the steps of the method are automated.

However, although the state of arteriosclerosis can be, to a certain degree, diagnosed with the above-described speed measurement, there has been no apparatus clinically applied for a circulatory system which efficiently analyzes the nature of arterial pulse wave propagation for the purpose of diagnosing a variety of vascular diseases or tension states of vascular walls.

SUMMARY OF THE INVENTION

Accordingly, a primary object of the present invention is to provide a method of and apparatus for automatically and non-invasively analyzing the fluctuation and distribution of the propagation time of arterial pulse waves. Such method and apparatus are based upon a fact that the degree of fluctuation in the propagation time of the arterial pulse wave from the center of the circulatory system (i.e. heart) to the periphery thereof, can serve as a diagnostic index of vascular wall tensions or an indication of diseases through a statistical analysis of such propagation times.

Another object of the present invention is to provide a method and apparatus for automatically and non-invasively analyzing the degree or rate of defectively-propagated contraction in addition to analyzing the fluctuation and distribution of the propagation time of the arterial pulse wave. Such method and apparatus are based upon a fact that the rate of generation of so-called "defectively-propagated contractions" (i.e. can be obtained on the basis of ascertained propagation time of an arterial pulse wave). Notably, such defectively-propagated contractions are determined where an effective pulse wave is not propagated to the periphery of the circulatory system notwithstanding the occurrence of cardiac muscle contraction, or where arterial pulse waves cannot distinctly propagate over a certain range or portion of the circulatory system.

In the present invention, in order to achieve the above-described objects, an "R-wave" contained in a detected electrocardiographic signal and the peak value (i.e. top or bottom peak) of an arterial plethysmographic signal sensed at a peripheral blood vessel portion, are detected for each pulse. From such detections, an R-wave signal and peak arterial pulse wave signal are generated, respectively. The time interval between the detected R-wave signal and detected peak pulse wave signal, $\Delta t_{R-P}$ is successively counted and is designated as the arterial pulse wave propagation time. On the basis of the computed arterial pulse wave propagation times, a statistical analysis is then performed with respect to the distribution of the arterial propagation times of an arterial pulse wave, and also with respect to the degree of defectively-propagated contractions, e.g. where peak arterial pulse signal is not detected between consecutively detected R-wave signals.

According to the present invention, circulatory diseases such as arteriosclerosis can be diagnosed by detecting the arterial pulse wave propagation time from the center of the circulatory system to the periphery thereof. Also, using the thus-obtained data regarding the variations in propagation time of arterial pulse waves for a predetermined time period, a more precise diagnosis of circulatory diseases can be conducted by the combination of arterial pulse wave propagation time variation data with data analysis of ECG or R-R interval fluctuation data.

Furthermore, on the basis of the degree or rate of defectively-propagated contractions, circulatory diseases indicated by varying degrees of arrhythmia, can be diagnosed.

Furthermore, it is expected that the present invention will contribute to the future development in application of the "arterial pulse wave propagation parameters" to clinical practice.

BRIEF DESCRIPTION OF THE DRAWINGS

FIG. 7 is a schematic diagram illustrating another modified example of a circuit according to the embodiment shown in FIG. 2.

DESCRIPTION OF THE PREFERRED EMBODIMENTS

Figure 1:
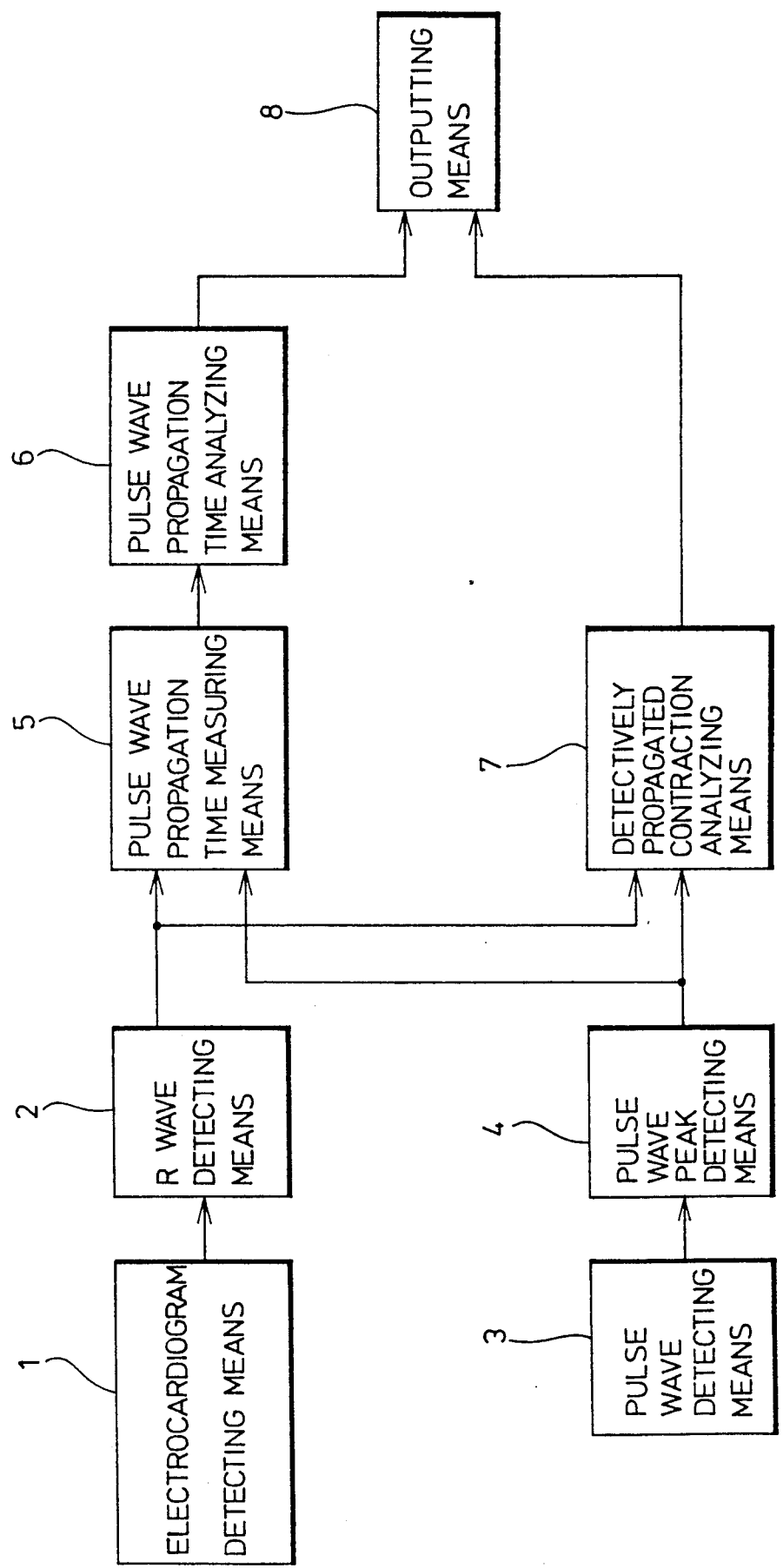
FIG. 1 is a block functional diagram illustrating the organizational structure of apparatus for analyzing the propagation of arterial pulse waves in accordance with the principles of the present invention.

FIG. 1 is a functional-block diagram illustrating the basic structure of apparatus for analyzing the propagation of arterial pulse waves according to the present invention. In general, the apparatus comprises a variety of components organized and cooperating with each other for "arterial pulse wave propagation time" determination and analysis.

In particular, means 1 is provided for detecting, amplifying and outputting electrocardiographic signals which have been introduced through electrodes attached to the breast or extremities of a patient. Means 2 is provided for detecting the R-wave component contained in the detected electrocardiographic signal, and outputting an R wave timing signal at the occurrence of this detection. Notably, the R-wave component of the QRS complex signal of an electrocardiographic signal, is an electrical signal representative of the contraction of the heart muscle of the left ventricle. An arterial pulse wave detecting means 3, such as plethysmograph or pulse oximeter, is provided and is attached to a peripheral blood vessel portion for the purpose of detecting an arterial pulse wave, i.e. arterial plethysmographic signal, which is representative of the flow of blood through the vessels, caused by variation in size thereof in response to the engorgement and displacement of blood. A means 4 is provided for detecting either the top or the bottom "peak" of the detected arterial plethysmographic signal (i.e. peak arterial pulse wave signal), and for outputting a pulse wave peak timing signal at the time of this detection. Means 5 is provided for measuring pulse wave propagation time, that is, successively measuring the time interval from after the time that R-wave timing signal has been generated, to the time of generation of the pulse wave peak timing signal. A pulse wave propagation time analyzing means 6 is provided for calculating the distribution of pulse wave propagation times. Also, a defectively-propagated contraction analyzing means 7 is provided, which detects the defectively-propagated contraction and analyzes the degree or rate of the same. Such defectively-propagated contractions are detected, for example, when a peak arterial pulse wave timing signal is not generated between the occurrence of consecutive R-wave signals. In addition, an outputting means 8 is provided for displaying or recording the result of the analysis performed by the two above-described analyzing means.

The R-wave detection means 2 successively detects R-wave signal components contained in an electrocardiographic signal and outputs an R-wave timing signal indicating the precise time at which each such detection occurs. Primarily, this device serves to determine when the origination of an arterial pulse wave (i.e. from the heart) occurs. On the other hand, the arterial pulse wave "peak" detecting means 4 detects the peak (i.e. either the extreme top or bottom) of the arterial plethysmographic signal, which is generated after and in response to the generation of the electrocardiographic signal. The arterial pulse wave peak detecting means 4 outputs the peak timing signal indicating the time of the "peak" detection. As a result of this procedure, the pulse wave propagation time (i.e. $\Delta t_{R-P}$) between the R-wave timing signal and the arterial pulse wave peak timing signal (also referred to as the R-P interval) is measured for every reoccurrence of the R-wave component in the QRS complex of the electrocardiographic signal generated.

The pulse wave propagation time analyzing means 6 thereafter analyzes over a predetermined time period, the distribution of each arterial pulse wave propagation time so as to provide a trend indication and histogram indication of the arterial pulse wave propagation time data, and also a calculated measure of the standard deviation of such data. The outputting means 8 then displays and/or records the results of the above-described analysis.

The defectively-propagated contraction analyzing means 7 detects a defectively-propagated contraction on the basis of a determination that no arterial pulse wave "peak" timing signal has been detected between detected R-wave timing signals. The defectively-propagated contraction analyzing means 7 also analyzes the degree of defectively-propagated contractions in terms of (i) the rate between the number of defectively-propagated contractions with respect to a predetermined time period, (ii) the rate between the detected number of arterial pulse waves, and/or (iii) the number of defectively-propagated contractions with respect to the heart rate. The analyzing means 7 enables the outputting means 8 to display or record the result of the analysis.

The arterial pulse wave generally takes anywhere in the range of 100–350 milliseconds to propagate through a length of 1 meter, whereas the usual time interval of the R-wave timing signals are in the range of 600–1000 milliseconds. Therefore, even when taking into consideration the time period required for the arterial pulse wave to appear in the origin of the ascending aorta in response to the generation of the R-wave signal, the arterial plethysmographic signal does not interfere with the electrocardiographic signal at the periphery, that is, before the generation of the next R wave signal, and is thereby assuredly distinguishable from the electrocardiographic signal.

Figure 2:
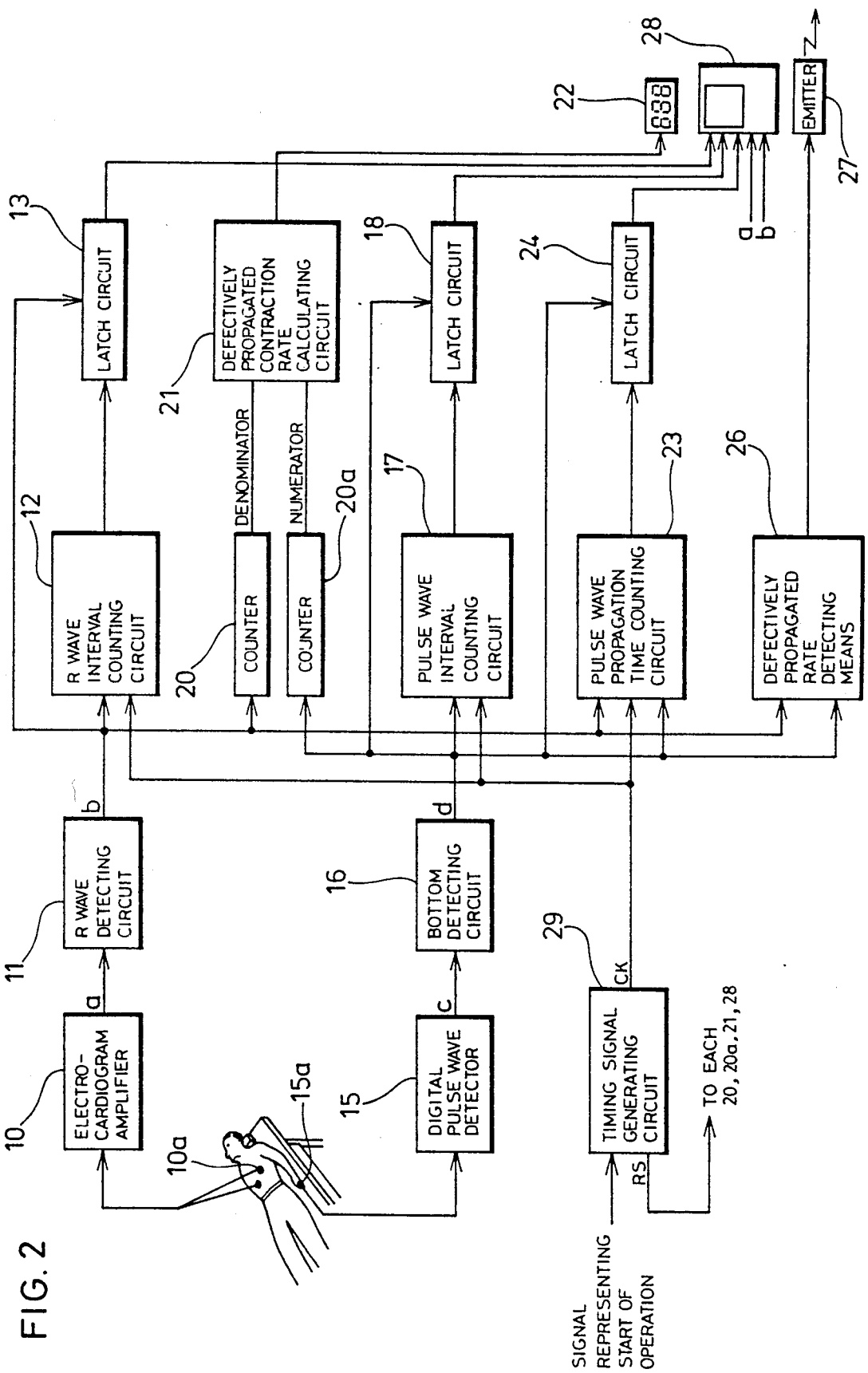
FIG. 2 is a block diagram illustrating the structure of the apparatus for analyzing the propagation of arterial pulse waves according to an embodiment of the present invention.
Figure 3A:
FIG. 3 is a graphical representation illustrating each operating waveform utilized in the method and apparatus of the present invention.
Figure 3B:
Figure 3C:
Figure 3D:

Referring to FIG. 2, there is shown in greater detail the structure of a circuit for use in the apparatus for analyzing the propagation of an arterial pulse wave in accordance with the principles of the present invention. Therein, reference numeral 10, in particular, represents an amplifier for amplifying the electrocardiographic signal which has been introduced into electrodes 10a attached to the breast. Reference numeral 11 represents an R wave detection circuit for detecting the R wave contained in the electrocardiographic signal (a) and for outputting an R wave timing signal (b) at the time of this detection. Reference numeral 12 represents an R wave interval counting circuit for counting clock pulses, CK, which have the interval of, for example, 100 μs, and which are supplied between the R wave timing signals (b) by a timing signal generating circuit 29. Reference numeral 13 represents a latch circuit for holding the counted value immediately before being reset every input of the R wave timing signals (b).

Reference numeral 15 represents a digital pulse wave detector for detecting the arterial plethysmographic signal sensed by a pickup 15a attached, for example, to the tip of a patient's finger. Reference numeral 16 represents a "bottom" (i.e. minimum level) peak detecting circuit for detecting the "bottom peak" of arterial pulse wave (c) shown in FIG. 3 in a differentiating manner, and for outputting a "bottom peak" arterial pulse timing signal (d) at the time of this detection. Reference numeral 17 represents a pulse wave interval counting circuit for counting the clock pulses, CK, which are produced between the "bottom peak" arterial pulse timing signals (d). Reference numeral 18 represents a latch circuit for holding the count immediately before resetting every input of the "bottom peak" arterial pulse timing signals (d).

Reference numeral 20 represents a counter for counting the number of the R-wave timing signals (b) (supplied by a timing signal generating circuit 29) until a reset signal RS is supplied, having, for example, an interval of two minutes. Reference numeral 20a represents a counter for counting a bottom timing signal (d) in the similar manner. Reference numeral 21 represents a circuit for calculating the rate of defectively-propagated contraction. Such a rate of "contraction propagation defects" is computed by performing division of a quotient (i.e. numerator/denominator) in such a manner that the count obtained by the counter 20 functions as a denominator while the count obtained by the counter 20a functions as a numerator. Reference numeral 22 represents a numeral-indicator for indicating, in the form of numerals, the rate of defects in contraction propagation.

As an alternative to the above-described embodiment, the defectively-propagated contraction rate calculating circuit 21 may have the output signal from the defectively-propagated contraction detecting circuit 26 counted by the counter 20a so as to make this count function as a numerator.

Reference numeral 23 represents a pulse wave propagation time counting circuit which counts the number of the clock pulses, CK, provided by circuit 29 as input during a time period measured from the time of input of the R-wave timing signal (b), to the time of input of the "bottom peak" arterial pulse timing signal (d). By the above-described operation of the "pulse wave propagation time counting circuit" 23, the time taken for the arterial pulse wave to propagate from heart to a finger, is accurately counted. Reference numeral 24 represents a latch circuit for latching (or holding) the count immediately before the input of the next R-wave timing signal (b).

Accordingly, by making the patient's fingertip a periphery, the present invention is effective in diagnosing the nature of the artery walls, from the aorta to the peripheral artery. Thus, the present invention can be used effectively to diagnose the arteriosclerosis.

Reference numeral 26 represents a defectively propagated contraction detecting circuit for outputting a pulse-formed signal representing the defectively-propagated contraction if any "bottom peak" pulse timing signal (d) is not input during the time period between consecutive R-wave timing signals (b). Reference numeral 27 represents an emitter (e.g. a visible or audible alarm) for indicating a defectively-propagated contraction in response to the presence of an input signal thereto, thereby providing detection of a defectively-propagated contraction.

Reference numeral 28 represents a cathode ray tube monitor which displays electrocardiographic waveform (a) and arterial pulse wave signal (c). Monitor 28 also displays a bar graph by converting the digital signal taken from the latch circuits 13, 18 and 24, into a graphical plot wherein an analog amplitude extends in the direction of the ordinate axis and time lapse of, for example, two minutes, is represented along the abscissa axis. The above-described components 22, 27 and 28 provide means for outputting the result of the analysis according to the present invention.

Operation of the above-described apparatus for analyzing the propagation of arterial pulse waves, will now be described with reference to FIGS. 3 and 4.

At the beginning of counting, when a signal representing start of operation is input to the timing signal generating circuit 29, the reset signal RS is output to reset each of the components 20, 20a and 21, and thereby generation of the clock pulses, CK, commences. The R-wave detecting circuit 11 detects the R-wave contained in the electrocardiographic signal (b), and provides as output, the R-wave timing signal (b) in a manner known in the art. The R-wave interval counting circuit 12 counts the number of the clock pulses CK during this interval, and causes the latch circuit 13 to hold as interval data between the R-waves (R-R), the count held by counter 12 at the time of the input of the next R-wave timing signal (b). Thereafter, counter 12 once again starts counting upon receiving the next R-wave timing signal (b) as input to counter The "bottom peak" pulse wave detecting circuit 16 detects the "bottom peak" of the input arterial plethysmographic signal (c), and provides as output the "bottom peak" pulse wave timing signal (d). The pulse wave interval counter 17 counts the number of the clock pulses CK during this interval, and causes the latch circuit 18 to hold as interval data between consecutive pulse waves, the count held by counter 17 at the time of the input of the next "bottom peak" timing signal (d). Thereafter, counter 17 once again starts counting upon receiving the next "bottom peak" timing signal (d) as input to counter 17.

The pulse wave propagation time counting circuit 23 counts the number of the clock pulses CK received upon the input of the R-wave timing signal (b) to counter 23, and causes the latch circuit 24 to hold as data representative of the pulse wave propagation time, the count held by counter 23 at the time of input of the bottom timing signal (d) to counter 23. Thereafter, counter 23 once again starts counting upon receiving the next R-wave timing signal as input to counter 23.

Figure 4:
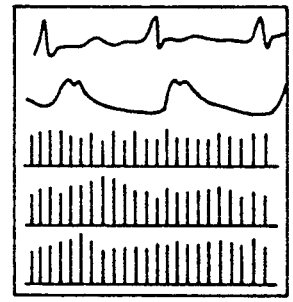
FIG. 4 is a graphical representation illustrating the state displayed on a cathode ray tube monitor according to the embodiment.

In the preferred embodiment, throughout the above-described operation, the cathode ray tube monitor 28 displays at a proper sweeping speed, the electrocardiographic signal (a), and the arterial pulse wave signal (c), as shown in FIG. 4. It also displays data regarding the R-wave interval, the arterial pulse wave interval, and the arterial pulse wave propagation time held by the latch circuits 13, 18 and 24. Such display is carrie out by successively converting the data into analog pulse wave forms in the direction of the ordinate axis corresponding to the respective data levels. As a result, they are successively displayed by shifting downwardly at a relatively lower speed.

The circuit 26 for detecting the defectively-propagated contraction causes the emitter 27 to instantaneously emit light upon the detection of every defectively-propagated contraction. Two minutes after the operation start, the reset signal RS is generated, and the defectively-propagated contraction rate calculating circuit 21 conducts the division, holds its result until the input of the next reset signal RS, and the numeral indicator 22 displays this result. On the other hand, as can be seen on the cathode ray tube monitor 28, over the two-minute interval the fluctuation of "biophysical parameters", e.g. (i) the R-wave interval, (ii) the pulse wave interval, and (iii) the pulse wave propagation time, are easily recognizable from the amplitude changes in the corresponding envelopes. In this regard, reference is made to FIG. 3, wherein the number of the analog pulse waveforms in the direction of the ordinate axis is reduced with respect to the actual number thereof.

Figure 5:
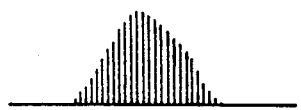
FIG. 5 is a graphical representation illustrating the state displayed on a cathode ray tube monitor according to another embodiment.

As indicated in FIG. 5, data held in the latch circuits 13, 18 and 24 can be provided to a CPU for statistical analysis. For example, in such an embodiment, data corresponding to each of the above-described parameters determined over a predetermined time interval is processed using statistical analysis so as to produce histogram data thereof. Thereafter, such histogram data is displayed on the cathode ray tube monitor 28. Accordingly, a histogram "on the R-wave timing intervals", and a histogram "on the peak timing intervals of plethysmographic signals" are computed, and the results provided thereby can be used by doctors, medical technicians and the like for the above-described medical diagnostic purposes. Furthermore, the average and the standard deviation with respect to such detected parameters, may be calculated and output in numerical form.

Figure 6:
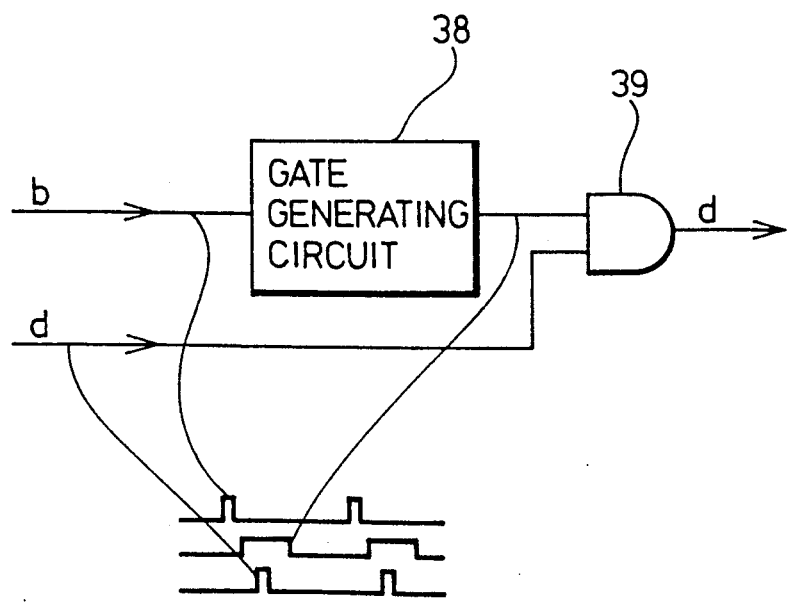
FIG. 6 is a schematic diagram illustrating a modified example of a circuit according to the embodiment shown in FIG. 2.

As shown in FIG. 6, the provision of a gate generating circuit 38 and AND gate 39 can be used to remove noise signals, such as the arterial pulse waves and the like, which do not depend upon the same heart beat. This circuit functions by allowing the pulse wave "peak" detecting means 16 to generate a pulse wave peak timing signal (d) only in response to a pulse wave "peak" which has been generated within a predetermined "gated" time period. Notably, over such a gated time period both the peak timing signal (d) and the R-wave timing signal (b) originated from the same heart beat, and thus are naturally correlated.

In connection with such a desired signal gating function, circuit 38 is provided for generating a gate which establishes a predetermined time period during which an arterial plethysmographic signal (c) is "triggered" by the R-wave timing signal (b) after a predetermined time delay, in order to ensure that the arterial plethysmographic signal (c) depends upon the same heart beat which has generated the triggering R-wave timing signal. The AND gate 39 is connected to the bottom detecting circuit 16, and the bottom peak pulse wave timing signal (b) is connected to one of the inputs to the AND gate 39 while pulse wave timing signal (d) is provided thereto as the other input. As a result of this configuration, the gate generating circuit of the present invention, in effect, disenables operation of the bottom detecting circuit 16 at times other than during this "gated" time period, since at all other times, the circuit 38 generates a reversed polarity signal with respect to the other input to the AND gate 39 of FIG. 6.

Notably, the electrodes 10a can be attached to the portions of a patient's body other than the breast. In a case where the electrodes 10a are attached to the breast as described above, they can be arranged to provide a known "impedance plethysmogram", i.e. by applying a high-frequency current of small amplitude to two of the electrodes 10a attached to the breast. However, as illustrated in FIG. 7, a circuit can be added to the circuit shown in FIG. 2. This would result in apparatus which is capable of confirming the correlation between the pulse wave propagation time (i.e. R-P time interval) and expiratory and inspiratory phases of a patient's respiratory cycle, and thereby provide a tool for diagnosing, for example, the elasticity of vascular walls.

In particular, such modification would involve the addition of the following circuits and devices: a respiratory wave pattern detecting circuit 31; an expiratory and inspiratory phase detecting circuit 32; an R-wave input timing determining circuit 33; arithmetic circuits 34 and 34a; a selection circuit 75; and numeral indicators 36 and 36a.

In such an embodiment shown in FIG. 7, the respiratory wave pattern detecting circuit 31 receives as input, a voltage signal detected by the electrodes 10a, and is fully capable of detecting respiratory wave pattern depending upon the thus-detected voltage change. The expiratory and inspiratory phase detecting circuit 32 is capable of detecting expiratory phase and inspiratory phase from the detected voltage signal. As shown in FIG. 2, the R-wave input timing determining circuit 33 receives as input, the R-wave timing signal (b), and is capable of determining whether or not both these two successive signals have been input to the expiratory phase or the inspiratory phase detecting circuit 32. The arithmetic circuits 34 and 34a calculate e.g. over a time period of three minutes, (i) the average of the maximum R-wave intervals (i.e. R-R interval) of the expiratory phase, (ii) the standard deviation of this average, (iii) the average of the maximum R-wave intervals (i.e. R-R interval) of the inspiratory phase, and (iv) the standard deviation of this average. The selection circuit 35 supplies the retained value in the latch circuit 13 shown in FIG. 2, to either the arithmetic circuit 34 or 34a. The selection circuit 35 carries out this supply function in response to the determination signal output from the R wave input timing determining circuit 33, or does not supply the same to both the arithmetic circuits 34 and 34a when the two successive R wave timing signals (b) are not present in expiratory phase and inspiratory phase. Finally, numeral-indicators 36 and 36a indicate to the operator, the above-described average and standard deviations of the expiratory phase and inspiratory phase, respectively, of the monitored respiratory cycle of the patient.

Usually, the R-R wave timing intervals in the expiratory phase and those in the inspiratory phase, are different from each other. However, according to another aspect of the present invention, it is now possible to diagnose the fluctuation of elasticity of vascular walls, and in turn, the tone of autonomic nerves such as vagal nerves governing the elasticity of vascular walls. This diagnosis method is carried out by first monitoring the R-R wave time intervals of both inspiratory and expiratory phase of the respiratory cycle of a patient. Notably, the R-R wave intervals associated with the expiratory and inspiratory phases, respectively, can be confirmed using numeral indicators 36 and 36a. Then, the respective R-R wave intervals are correlated to the pulse wave propagation time (i.e. the R-P interval), so as to correlate data from which the elasticity or tone of vascular walls can be diagnosed.

While the particular embodiments shown and described above have been proven to be useful in many applications involving the biophysiological instrumentation arts, further modifications of the present invention herein disclosed will occur to those skilled in the art to which the present invention pertains and all such modifications are deemed to be within the scope and spirit of the present invention defined by the following claims.

What is claimed is:

1. An apparatus for analyzing the propagation of arterial pulse waves in a patient, comprising:

means for detecting an electrocardiographic signal with electrodes adapted to be attached to breast or extremities of said patient;

means for detecting an R-wave from said detected electrocardiographic signal, and generating an R-wave timing signal at the time of said R-wave detection;

pulse wave detecting means adapted to be attached to a peripheral blood vessel portion of said patient, and being capable of detecting an arterial plethysmographical signal;

means for detecting a pulse wave peak of said detected arterial plethysmographical signal, and generating a peak timing signal at the time of said pulse wave peak detection;

means for determining an arterial pulse wave propagation time on the basis of said R-wave timing signal and said peak timing signal, said pulse wave propagation time determination involving successively measuring a time interval between the generation of said R-wave timing signal and the generation of said peak timing signal;

pulse wave propagation time analyzing means for analyzing a distribution of individual pulse wave propagation times for a predetermined period and the fluctuation between individual pulse wave propagation times and for calculating the standard deviation of the pulse wave propagation times; and outputting means for displaying or recording the result of said analysis conducted by said means for analyzing the pulse wave propagation time.

2. An apparatus for analyzing the propagation of arterial pulse wave according to claim 1, which further comprises means for detecting the occurrence of defectively-propagated contractions, and further analyzing the degree or rate of defectively-propagated contractions on the basis of whether any peak timing signals have not been generated between consecutive signals of said R-wave timing signals during a predetermined time period.

3. An apparatus for analyzing the propagation of arterial pulse wave according to claim 1, which further comprises R-wave interval measuring means for determining the interval between successive R-waves, the R-wave interval measuring means being operatively coupled to the R-wave detecting means, and which further comprises pulse wave interval measuring means for determining the interval between pulse wave peaks of successive detected arterial plethysmographical signals, the pulse wave interval measuring means being operatively coupled to the pulse wave peak detecting means, and wherein said outputting means displays or records a histogram on the R-wave timing intervals, and a histogram on the peak timing intervals of said arterial plethysmographic signals.

4. An apparatus for analyzing the propagation of arterial pulse waves according to claim 1, which further comprises means for generating a gate which establishes a predetermined time period in response to the generation of an R-wave timing signal, the gate generating means being coupled to the pulse wave peak detecting means and the R-wave detecting means and providing an output signal representative of a pulse wave peak timing signal detected during the predetermined period of time.

5. An apparatus for analyzing the propagation of arterial pulse wave according to claim 1, which further comprises:

at least one electrode adapted to be attached to the breast of the patient, the electrode providing an output signal indicative of the expiratory and inspiratory phases of the respiration of the patient;

a respiratory wave pattern detecting means, the respiratory wave pattern detecting means being coupled to the electrode and detecting a respiratory wave pattern of the respiration of the patient in response to the output signal of the electrode and providing a detection signal;

expiratory and inspiratory phases detecting means capable of detecting the expiratory phase and inspiratory phase from the detection signal from said respiratory wave pattern detecting means;

R-wave interval analyzing means capable of measuring intervals between successive R-waves and correlating the intervals to the detected expiratory and inspiratory phases; and outputting means for indicating or recording said R-wave interval of said expiratory phase and that of said inspiratory phase measured and correlated by said R-wave interval analyzing means.

6. Method for analyzing the propagation of arterial pulse waves in a patient, comprising the steps of:

(a) detecting an electrocardiographic signal using electrodes adapted to be attached to the breast or other extremities of said patient;

(b) detecting an R-wave from said detected electrocardiographic signal, and generating an R-wave timing signal at the time of said R-wave detection;

(c) detecting an arterial plethysmographical signal at a peripheral blood vessel portion of said patient;

(d) detecting a pulse wave peak of said detected arterial plethysmographical signal, and generating a peak timing signal at the time of said pulse wave peak detection;

(e) determining an arterial pulse wave propagation time on the basis of said R-wave timing signal and said peak timing signal, said pulse wave propagation time determination involving successively measuring a time interval between the generation of said R-wave timing signal and the generation of said peak timing signal;

(f) analyzing over a predetermined period of time, detected arterial pulse wave propagation times and the fluctuation between individual pulse wave propagation times, and computing a distribution of individual pulse wave propagation times and calculating the standard deviation of the pulse wave propagation times; and (g) displaying or recording the results of said analysis performed by step (f).

7. The method according to claim 6, which further comprises, detecting the occurrence of defectively-propagated contractions, and further analyzing the degree or rate of said defectively-propagated contractions on the basis of whether, for a number of R-waves propagated over a predetermined time period, any peak timing signals have not been generated between consecutive signals of said R-wave timing signals.

* * * * *